(12) United States Patent
Paakkinen

(10) Patent No.: US 6,729,189 B2
(45) Date of Patent: May 4, 2004

(54) METHOD AND APPARATUS FOR MEASURING PACKING PROPERTIES

(76) Inventor: Antti Paakkinen, Aurakatu 6 as. 9, Mikkeli (FI), 50190

( * ) Notice: Subject to any disclaimer, the term of this patent is extended or adjusted under 35 U.S.C. 154(b) by 0 days.

(21) Appl. No.: 10/292,229

(22) Filed: Nov. 12, 2002

(65) Prior Publication Data

US 2003/0089178 A1 May 15, 2003

Related U.S. Application Data

(63) Continuation of application No. PCT/FI01/00446, filed on May 10, 2001.

(30) Foreign Application Priority Data

May 12, 2000 (FI) .............................................. 20001129

(51) Int. Cl.$^7$ ................................................. G01N 3/08
(52) U.S. Cl. ............................. 73/824; 73/813; 73/818; 73/841
(58) Field of Search ............................. 73/9, 84, 432.1, 73/794, 795, 813, 815, 818, 824, 841; 366/56

(56) References Cited

U.S. PATENT DOCUMENTS

| | | | |
|---|---|---|---|
| 2,972,249 A | 2/1961 | McRae et al. ............... 366/56 |
| 3,461,717 A | 8/1969 | Dunlap et al. ................. 73/84 |
| 3,465,575 A | * 9/1969 | Krepes ..................... 73/54.32 |
| 3,478,572 A | * 11/1969 | McRae et al. ................... 73/9 |
| 3,767,351 A | * 10/1973 | Blaser ........................ 425/432 |
| 3,925,000 A | * 12/1975 | Haberle ....................... 425/422 |
| 3,986,566 A | * 10/1976 | Hamilton ..................... 173/31 |
| 3,998,090 A | * 12/1976 | Wislocki .................... 73/12.12 |
| 4,784,206 A | * 11/1988 | Sauerman et al. ............. 164/18 |
| 4,794,799 A | * 1/1989 | Paakkinen ..................... 73/803 |
| 4,930,346 A | * 6/1990 | Paakkinen et al. ......... 73/54.31 |
| 4,942,768 A | * 7/1990 | McRae ........................ 73/795 |
| 5,036,709 A | * 8/1991 | McRae ........................ 73/841 |
| 5,275,056 A | 1/1994 | Hamilton et al. ............. 73/794 |
| 5,323,655 A | * 6/1994 | Eagan et al. ............... 73/432.1 |
| 5,456,118 A | * 10/1995 | Hines et al. .................. 73/818 |
| 5,606,133 A | * 2/1997 | Hines et al. .................. 73/824 |
| 5,698,789 A | * 12/1997 | Lainio et al. ................. 73/824 |
| 5,817,946 A | * 10/1998 | Brovold ........................ 73/818 |
| 5,824,913 A | * 10/1998 | Pyle ........................... 73/818 |
| 5,911,164 A | * 6/1999 | McRae ........................ 73/815 |
| 5,916,504 A | * 6/1999 | Edwards et al. .............. 264/71 |
| 5,939,642 A | * 8/1999 | King et al. ................... 73/813 |
| 6,026,692 A | 2/2000 | Brovold ........................ 73/818 |
| 6,205,864 B1 | * 3/2001 | Vialletel et al. ............... 73/824 |

FOREIGN PATENT DOCUMENTS

| | | | | |
|---|---|---|---|---|
| DE | 1598408 B2 | 3/1971 | | |
| DE | 2147385 A | * 11/1972 | ............. B28B/1/08 |
| FI | 96243 C | 5/1996 | | |

* cited by examiner

Primary Examiner—Hezron E. Williams
Assistant Examiner—David A. Rogers
(74) Attorney, Agent, or Firm—Harrington & Smith, LLP

(57) ABSTRACT

Subject of the invention is a method to measure the compaction properties of soil and other similar masses. A mass specimen is placed in a cylinder. The mass specimen is then pressed with standard pressure between an upper platen and a lower platen, and the height of the specimen is measured. Also subject of the invention is a device to measure the compaction properties of soil and other similar masses. Characteristic to the method and apparatus according to the invention is the fact that there is a specimen cylinder (2) attached to the frame (1) to be rotated mainly with respect to its central axis.

13 Claims, 2 Drawing Sheets

METHOD AND APPARATUS FOR MEASURING PACKING PROPERTIES

This application is a continuation of and claims priority from International Patent Application No. PCT/FI01/00446, having an international filing date of May 10, 2001 and which claims priority from Finnish Patent Application No. 20001129, filed May 12, 2000.

BACKGROUND OF THE INVENTION

A subject of the invention is a method to measure compaction properties of masses of the soil and other masses of similar kind. A mass specimen in a cylinder is pressed with standard pressure between an upper platen and a lower platen and the height of the specimen is measured in this method. A subject of the invention is also a device to accomplish earlier mentioned task. There is a frame, a specimen cylinder and a pressing device with an upper platen and a lower platen to be pressed against a specimen and placed in an angle with respect to the central axis of the specimen cylinder in this device.

To measure the change in density of masses of the soil and other masses of the kind like bituminous asphalt, the method of gyratory compaction is used and a device for gyratory compaction is needed. In already known methods of gyratory compaction the compaction is, in most cases, provided by pressing upper and lower platens of a cylindrical mould with standard pressure and rotating the other end of the cylinder abount a point, other than the central axis of the cylinder in a circular manner (so called gyratory-motion). Pressure and gyratory-motion create continuous sine-shaped reversal cross sectional deformation. Because of the pressure and the cross sectional deformation the soil particles of the specimen move with respect to each other and seek their way closer to each other so that compaction occurs and it densifies. Compaction and the growth in density are related to the properties of the material and the amount of cross sectional deformation. Thus, the change in density depends also on the number of gyrations. The number of gyrations (the angular velocity) as well as the temperature of the specimen are kept in the sphere at a test temperature according to the standards for the mixture in question during the compaction test. As the result the test provides the density corresponding to a known standard pressure and angle as the function of gyratory-motions. The shape and the location of the curve describing the densifying process depend on the material to be densified and its properties, the size of its particles and while mixtures are in question, the composition of separate components. Measured densifying properties can be utilized to determine the optimal composition and preparing methods for materials, like asphalt, used in earth and road works.

There are some various mechanisms known today that create gyratory compaction motion adjustable to a gyratory compaction device. Gyratory compaction motion in those devices is provided either by moving one end of the specimen cylinder in a circular manner (gyratory-motion) or by inclining the upper platen and the lower platen of the specimen cylinder on various sides by means of a rod adjusted in the middle of them with gyratory motions.

Measurements of the compaction properties by known methods and devices of gyratory compaction can be accomplished in a functional way, but their mechanisms that create the suitable gyratory compaction motion are complicated in construction and economically expensive and intricate to make because of the high requirements of precision.

SUMMARY OF THE INVENTION

The purpose of the invention is to create a method and a device to measure compaction properties of masses of the soil and other masses of the kind to prevent earlier mentioned problems.

The purpose of the invention is achieved by the method and the device, characteristic of which is what has been presented in the claims.

Characteristic to the method according to the invention is the fact that the mass specimen in the gyratory compaction device is rotated round the central axis that is incliner with respect to the upper and lower platen, thus generating densifying cross sectional deformations. When rotating a mass specimen about the central axis that has been rigidly supported the gyratory compaction devices may be relatively simple and exact. Manufacturing costs will be advantageous because of the simplicity of the devices.

Characteristic to the device according to the invention is the fact that the specimen cylinder has been attached to the frame of the gyratory compaction device mainly to be rotated with respect to its central axis. Constructions of the specimen cylinder which has been attached to be rotated with respect to its central axis as well as the upper and lower platens in the upper and lower part can be designed to be simple, rigid and very exact.

In an advantageous application of the device according to the invention a specimen cylinder has been mounted on bearings into a supporting construction, which has been attached to the frame in the way that the lower part is turnable. Because of the turnable attachment of the lower part, inclining of the specimen cylinder can be successfully carried out because of the simple exact and reliable construction.

In the second advantageous application of the device according to the invention there is a regulating device between the upper part of the supporting construction and the frame to incline the supporting construction and the specimen cylinder to a desired position. By means of the regulating device the specimen cylinder can be inclined to the desired position exactly and reliably.

In the third advantageous application of the device according to the invention a rotating device has been connected to the specimen cylinder in order to rotate the specimen cylinder and the specimen during the compaction. By means of the rotating device connected to the specimen cylinder, the specimen cylinder and the specimen can be rotated according to the demands of the test simply and advantageously.

In the fourth advantageous application of the device according to the invention a rotating device has been connected to the upper platen to rotate the upper platen and the specimen during the compaction. By rotating the upper platen, sliding between the specimen and the upper platen is prevented, and advantageous rotating motion with respect to the specimen is guaranteed, thus making the gyratory compaction device reliable and suitable for many various specimen materials.

In the fifth advantageous application of the device according to the invention a rotating device has been connected to the lower platen to rotate the lower platen and the specimen during the compaction. By rotating the lower platen the undesirable sliding of the lower platen and the specimen is prevented, thus making the gyratory compaction device function exactly and reliably.

In the sixth advantageous application of the device according to the invention the upper part of the specimen cylinder has been supported to the frame by at least two rolls mounted in bearings to the frame. Because of the support organised with the rolls, the mounting in bearings is simple, without clearances and rigid.

In the seventh advantageous application of the device according to the invention the rolls have been mounted in bearings to be moved with a regulating device to incline the specimen cylinder to a wanted position. Because of the rolls, mounted in bearings with regulating device, the specimen cylinder can be inclined in a functional way advantageously and exactly to the desired position.

In the eighth advantageous application of the device according to the invention the lower part of the specimen cylinder has been supported from the inner surface to the lower platen to mount in bearings the lower part of the specimen cylinder to the frame. Because of the support of the lower platen of the specimen cylinder, the mounting in bearings of the specimen cylinder is simple and economical to make and the lower platen can be used to rotate the specimen cylinder, thus, avoiding the need of a separate rotating device for the specimen cylinder.

BRIEF DESCRIPTION OF THE DRAWINGS

In the following the invention is presented more detailed referring to enclosed drawings, in which in FIG. 1 there is a cross section figure of the gyratory compaction device according to one method according to the invention from side, and in FIG. 2 there is a cross section figure of the gyratory compaction device according to another method according to the invention.

DETAILED DESCRIPTION OF THE INVENTION

Figure 1:
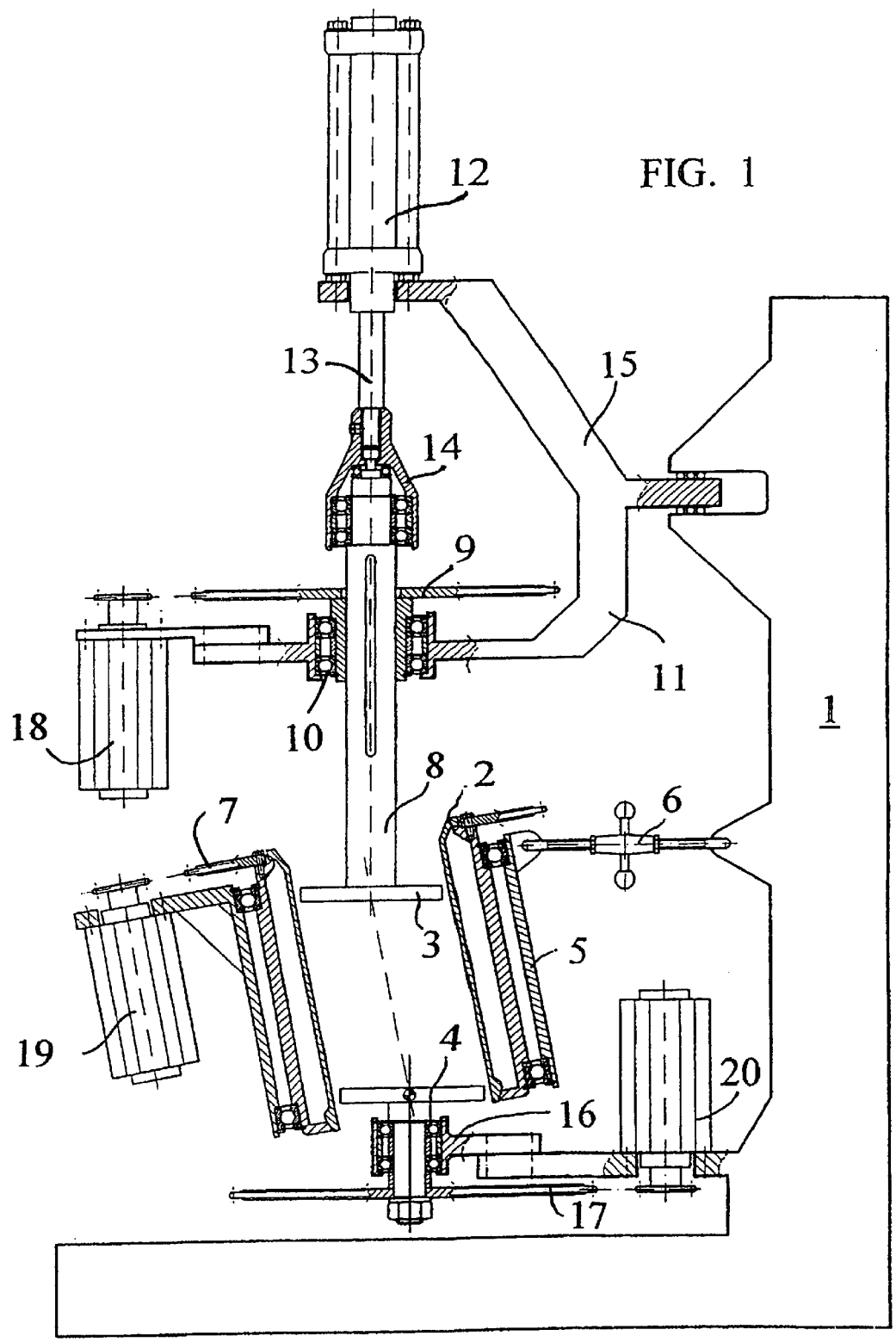

According to FIG. 1 there is the frame 1, the specimen cylinder 2, the upper platen 3 of the specimen cylinder, the lower platen 4 of the specimen cylinder, the control construction 5 of the specimen cylinder, the regulating device 6 of the angle of incline of the specimen cylinder, rotating device 7 of the specimen cylinder, the shaft 8 of the upper platen, the rotating device 9 of the shaft of the upper platen, bearings 10 of the shaft of the upper platen, the moving attachment 11 of the shaft of the upper platen and its drive mechanism, the pneumatic cylinder 12 functioning as a pressing device, the moving end 13 of the pneumatic cylinder, the connecting organ 14 of the pneumatic cylinder, the fixing shoulder 15 of the pneumatic cylinder, bearings 16 of the lower platen and the rotating device 17 of the lower platen in the gyratory compaction device. Furthermore there are drive mechanisms 18,19 and 20 to rotate the upper platen, the specimen cylinder and the lower platen and also other earlier known connecting parts and mechanical components to connect various parts of the gyratory compaction device with one another in due form.

The frame 1 of the gyratory compaction device according to FIG. 1 has been made of steel plates and using various existing mechanical and connecting components like groove ball bearings and bolts. Plate parts like various fixing constructions and housing have been made by bending and cutting the plate and by using various connecting methods. The construction of the frame is earlier known so that the outer shape of the frame resembles frames of earlier known gyratory compaction devices.

The specimen cylinder 2 has been connected to the rotating inner cylinder, mounted in bearings to the control construction 5, in a removable way. The control construction has been fixed in a lower part of the solid part turnable to the frame 1. In the application according to FIG. 1 the specimen cylinder 2 is a cylindrical object made of a steel pipe slightly broaden in a suitable way from the upper and lower ends. The specimen cylinder locks by means of its broadened parts to the shoulders of the upper and lower ends of the inner cylinder of the control construction, when the specimen cylinder is placed inside the control construction. There is a movable end of the specimen cylinder fixed in the upper part of the control construction with the bolt of the regulating device 6, and thus the angle of the specimen cylinder and its central axis is adjustable by turning the bolt of the regulating device. The rotating device in the upper part of the specimen cylinder consists of a primary wheel and a secondary wheel and a chain or a belt adjusted between them. The smaller primary wheel of the rotating device has been adjusted to the end of the shaft of the drive mechanism 19 fixed to the control construction. The purpose of the rotating device of the specimen cylinder is to rotate the specimen cylinder as required.

The upper platen 3 of the specimen cylinder 2 is a flange made of the shaft 8. It has been connected to the shaft in the way that the upper platen can be rotated inside the specimen cylinder by rotating the shaft. The diameter of the upper platen is the same as the inner diameter of the specimen cylinder, however adjustable inside the cylinder. The shaft 8 has been connected by means of bearings 10 so that it can be rotated and moved vertically relative to the construction 11 which is fixed to the frame 1 so that it can be moved sideways. Because of it this construction the shaft and the upper platen adjusted inside the specimen cylinder move sideways with the upper part of the specimen cylinder. To rotate the shaft 8 it has been connected with a secondary wheel of the rotating device 9 connected to the shaft in rotating direction but moving in axial direction.

A joint element 14 has been connected with bearings to the upper end of the shaft 8. This element allows rotation of the shaft, but transmits the motions of the moving end 13 of the pneumatic cylinder 12 that has been connected to the shoulder 15 of the attachment 11 moving sideways to the shaft and the upper platen. Thus, the shaft 8 and the upper platen 3 can be moved with the pneumatic cylinder 12 functioning as a pressing device vertically inside the specimen cylinder 2 in a functional way. Because of the attachment 11 moving sideways the pressing device can be moved as wanted according to the angle of the specimen cylinder.

Pneumatic cylinder 12 forms a lineary moving operating device which moves vertically the upper platen 3 and the shaft 8 functioning as a pressing device. In the application according to FIG. 1 the pneumatic cylinder 12 is a double-acting pneumatic cylinder. By means of its moving end 13 the upper platen can be moved up and down and press against the specimen. The pressing force is maintained constant according to the dehsifying test by regulating the pressure of the pneumatic cylinder.

There are grooves for the bearings on the shaft 8 of the upper platen 3, where the axial shoulders (not presented in FIGS. 1 and 2) of the corresponding shape are locked preventing the sliding of the rotating side of the bearing and of the secondary wheel of the rotating device on the axis in rotating direction. Mounting in the bearings 10 has been accomplished in other parts in earlier known methods according to FIG. 1 with two radial bearings attached to the moving attachment 11 which are movable sideways and vertically at a certain distant from one another.

Moving attachment 11, which is movable sideways, consists of a part, fixed movable sideways to the frame and including shoulders for bearings 10 of the shaft 8 and for pneumatic cylinder 12. The moving attachment 11, movable sideways, has been connected with drive mechanism 18 of the shaft 8. In the end of the shaft of the drive mechanism 18 there is the primary wheel of the rotating device 9.

In the upper part of the shaft 8 a connecting element 14 has been mounted in bearings to connect the shaft 8 with the pneumatic cylinder 12 that functions as a pressing device. There are two radial bearings mounted vertically at a suitable distant from one another and an axial bearing to transmit the vertical motion of the moving end 13 of the pneumatic cylinder to the upper platen 3 by means of the shaft 8. The connecting element 14 is a component designed to the shape of the end of the shaft 8 and to which the earlier mentioned bearings are adjusted.

Figure 2:
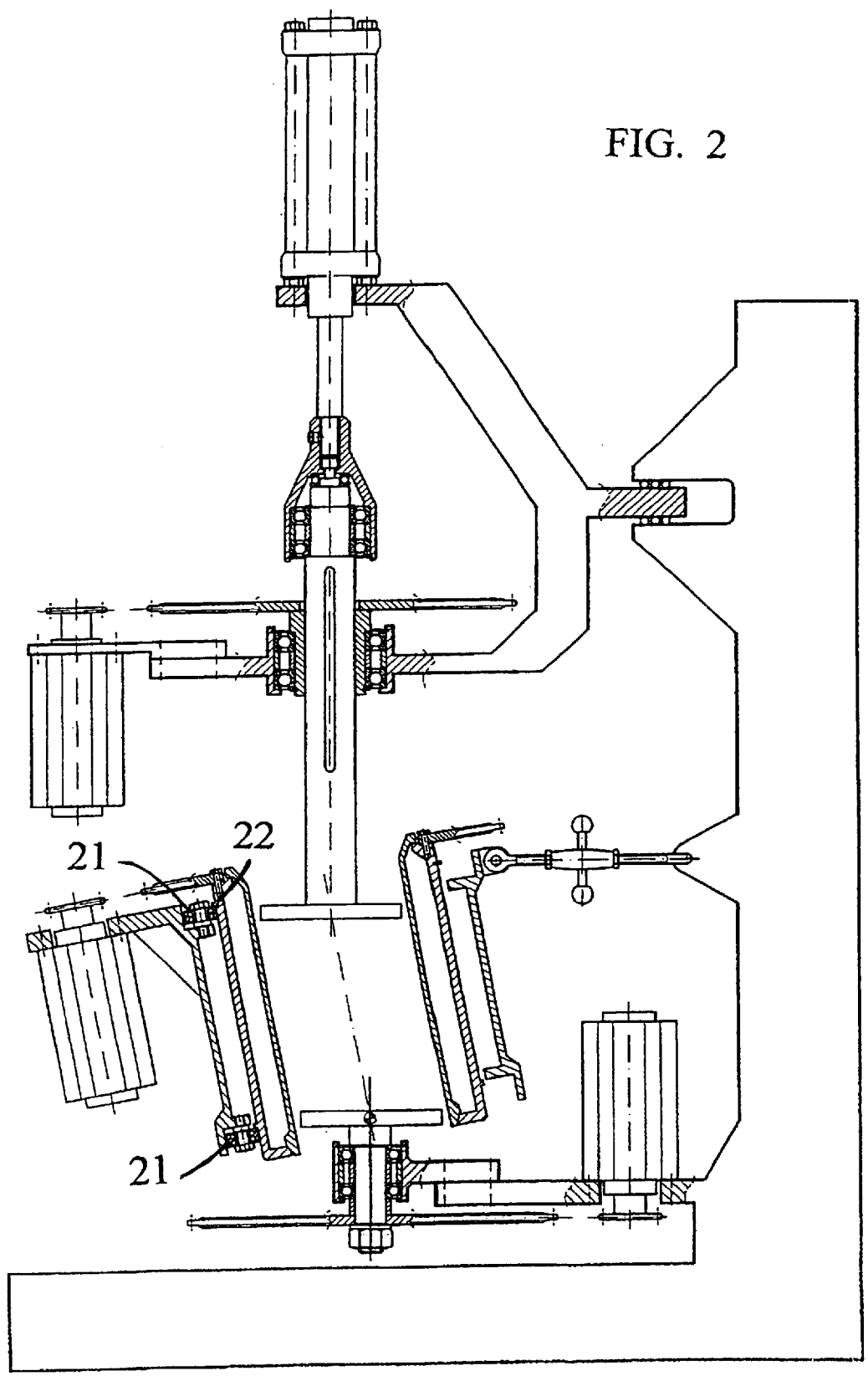

The lower platen 4 has been connected to the frame 1 with a vertical shaft and bearings 16 in the way such that the lower platen is placed in the lower part of the specimen cylinder according to the FIG. 1 and 2 inside the specimen cylinder. The lower platen is by size and shape a flange like element equivalent to the upper platen and, it has been made of the same steel element as the shaft of the lower platen. The other end of the shaft of the lower platen reaches the lower part of the bearings. There is the secondary wheel of the rotating device 17 of the lower platen adjusted with bolts to the end of the shaft. The primary wheel of the rotating device has been connected to the end of the shaft of the drive mechanism 20 of the rotating device of the lower platen. By means of the rotating device and the drive mechanism 20 connected to the lower platen 4 the lower platen can be rotated with the specimen cylinder 2 and the upper platen 3. Because of the construction described above the specimen cylinder, the upper platen and the lower platen form a unit, inside of which a specimen of mass of desired size and according to the dimensions of the specimen cylinder can be placed.

The regulating device 6 of the angle of incline of the specimen cylinder in the application according to FIG. 1 is a bolt organ which is rotated by fingers, and the length of which changes according to the direction of rotation of the bolt organ. The regulating device is self locking, thus, the length and the angle of incline of the control construction 5 of the specimen cylinder stays in adjusted position without other locking elements. The regulating device has been adjusted to the frame by a turnable fixing element in the fixed end. The fixing of the moving end to the control construction of the specimen cylinder is turnable so that the inclining mechanism of the control construction of the specimen cylinder and the regulating device would function as needed.

Drive mechanisms of the specimen cylinder, the upper platen and the lower platen are, in the application according to FIG. 1, alternating current motors. Transmission from the primary wheels on the shafts of the drive mechanisms to the secondary wheels has been accomplished by chain or belt transmission. Speed of rotation and the gear ratio (i.e. the relationship between the size of the primary and secondary wheels of all drive mechanisms) is the same so that the speed of rotation of the specimen cylinder, the upper platen and the lower platen would be as equivalent as possible.

In the gyratory compaction device according to another method according to the invention presented in FIG. 2, the frame, the specimen cylinder and the upper platen are equivalent to those in the application in FIG. 1. Also the rotating device, drive mechanism and the fixing elements of the specimen cylinder, the upper platen and the lower platen as well as the regulating device between the upper part of the control construction and the frame are equivalent to those presented in the application according to FIG. 1. The strut of the specimen cylinder is, however, different. It is organised by means of rolls 21 supporting the inner cylinder of the control construction and mounted in bearings in every 120 degrees seen from above around the specimen cylinder. The rolls supporting the inner cylinder are adjusted according to FIG. 2 to the outer cylindrical construction of the control construction 22 in the place of the upper and lower part of the specimen cylinder. Thus, the inner cylinder of the control construction between them and the removable specimen cylinder adjusted to it are to be rotated with respect to their central axis according to the invention.

Preparing stages for a specimen of mass in starting the compaction test with a gyratory compaction device according to FIGS. 1 and 2 are accomplished according to earlier known methods. The actual compaction of the specimen is realized by compressing the specimen by a pneumatic cylinder 12 and rotating the cylinder, the upper platen and the lower platen while the specimen stays inside the specimen cylinder. During the test the specimen cylinder and the specimen itself are rotated according to the method according to the invention about its own central axis, for instance for a pre-set number of gyrations or until target change in density has been achieved. The compaction pressure stays constant during the rotation. Compaction pressure and the other parameters can be chosen according to the regulations in standards for the material of the specimen. The rotation of the mass specimen with the inclined cylinder and the horizontal upper platen and the lower platen provides at different points according to radius a vertical sine-shaped reversal cross sectional deformation. This provides densifying accordingly to the earlier known gyratory compaction devices. The number of cycles of the specimen cylinder corresponds to the number of cycles like gyratory motions of the earlier known devices. Therefore, by means of the gyratory compaction device according to the invention, the compaction behavior of bituminous and concrete mass samples can be determined as could be done with known gyratory compaction devices.

Construction and materials of various parts and the joints between them of the gyratory compaction device according to the invention can vary. The frame 1 can be accomplished in very many various ways. As distinct from the application in FIGS. 1 and 2 it can be realized of various kinds of mould elements or metallic parts using various kinds of connecting and/or fixing elements. Also the shape and dimensions of the frame may vary for instance depending on the construction of various devices and mechanical elements.

The specimen cylinder 2 of the gyratory compaction device according to the invention can be realized by many other ways and also of other material than steel. It may be made of aluminium or plastic in some other application. The dimensions, shapes and fixing methods of the specimen cylinder to the frame may differ from the applications according to FIGS. 1 and 2. The specimen cylinder can be supported at the lower part with a lower platen only inside the cylinder in the third application modified from the application according to FIG. 2. In this case the fixing of the lower part of the specimen cylinder does not need other separate fixing elements, but the turnable fixing to the lower platen can be accomplished for instance with a lower platen adjusted turnable without clearance and sliding inside the specimen cylinder.

The upper platen 3 and the construction of the rotating device 7 connected to it can also vary. The upper platen may be a separate part, adjusted vertically movable with respect to the shaft 8. This part is moved by means of a pivot going through the shaft in vertical direction and rotates with the shaft and has been mounted in axial bearings to the moving end 13 of the pneumatic cylinder.

In the place of the pneumatic cylinder functioning as a pressing device of the upper platen some other lineary moving device like a hydraulic cylinder may be used. Pressing mechanism can be alternatively accomplished by means of a rack bar or a bolt. Control of pressing force is in that case, however, more complicated than when using a hydraulic or pneumatic system. The constructions of the lower platen, the shaft of the lower platen and the rotating device of the lower platen can also differ from the construction according to FIGS. 1 and 2. The lower platen can be adjusted to the end of a shaft of a reduction gear fixed to the frame and driven by a motor. Power transmission for the rotating devices can be accomplished also some other way than according to the example applications in FIGS. 1 and 2. For power transmission gear drive or friction drive can be used. As drive motors any drive mechanism providing rotating motion such as electric motors, hydraulic motors or pneumatic motors can be used in various application according to the invention.

All the same measurements as with earlier known methods and devices for measuring compaction properties mentioned above can be accomplished with the method and device according to the invention. The size of the specimen cylinder can be chosen according to standards, therefore, the method and the device can be applied for materials of various particle sizes. Control of temperature and the pressing force of the upper platen and the lower platen can be chosen to meet various requirements. All necessary equipment for control, regulation and measurements can be adjusted to the device according to the invention, in order to realize necessary measurement according to various requirements and standards. The method and the device according to the invention can be applied to many other researches and product development projects where it is not necessary to use amounts of specimen and/or specimen cylinders according to standards of today.

The invention is not limited to above presented applications but can vary within the framework of inventional idea according to the claims.

What is claimed is:

1. A method for measuring the compaction properties of a specimen of soil and other masses of similar kind utilizing a cylinder with a central axis, an upper platen, and a lower platen, the method comprising the steps of:
    placing a mass specimen in said cylinder;
    rotating said cylinder and mass specimen about said cylinder's central axis that is inclined with respect to said upper platen and said lower platen;
    pressing said mass specimen between said upper platen and said lower platen using standard pressure thus providing deformations that increases the density the mass specimen; and
    measuring the height of said mass specimen as an indicator of the compaction property of the mass specimen.

2. A device for measuring compaction properties of masses of a specimen of soil and other masses of similar kind, comprising:
    a frame, a specimen cylinder, a pressing device, an upper platen and a lower platen;
    the upper platen and the lower platen are adapted to be pressed with a pressing device against the specimen; and
    wherein the specimen cylinder has a central axis which is angled relative to a vertical axis, wherein the upper and lower platens are inclined with respect to the central axis of the specimen cylinder, and wherein the specimen cylinder is attached to the frame to be rotated mainly with respect to its central axis.

3. A device according to the claim 2, further comprising a rotating device connected to the specimen cylinder in order to rotate the specimen cylinder and the specimen during the compaction.

4. A device according to the claim 2, further comprising a rotating device connected to the upper platen in order to rotate the upper platen and the specimen during the compaction.

5. A device according to the claim 2, further comprising a rotating device connected to the lower platen in order to rotate the lower platen and the specimen during the compaction.

6. A device according to the claim 2, in which the specimen cylinder is connected at an upper part of the specimen cylinder to the frame by at least two rolls.

7. A device according to the claim 2, in which a lower part of the specimen cylinder is connected only to the lower platen to connect the lower part of the specimen cylinder to the frame.

8. A device according to the claim 2 wherein the upper and lower platens are substantially horizontal.

9. A device for measuring compaction properties of masses of a specimen of soil or other masses of similar kind, comprising:
    a frame, a specimen cylinder, a pressing device, an upper platen and a lower platen;
    the upper platen and the lower platen are adapted to be pressed with a pressing device against the specimen;
    wherein the upper and lower platens are inclined with respect to a central axis of the specimen cylinder, wherein the specimen cylinder is attached to the frame to be rotated mainly with respect to its central axis;
    and further comprising:
    a control construction which has a lower part that is fixed and is turnable relative to the frame; and
    wherein the specimen cylinder is mounted in bearings to the control construction.

10. A device according to the claim 9, further comprising a regulating device placed between an upper part of the control construction and the frame in order to incline the control construction and the specimen cylinder to a desired position.

11. A device for measuring compaction properties of masses of a specimen of soil and other masses of similar kind, comprising:
    a frame, a specimen cylinder, a pressing device, an upper platen and a lower platen;
    the upper platen and the lower platen are adapted to be pressed with a pressing device against the specimen;
    wherein the upper and lower platens are inclined with respect to a central axis of the specimen cylinder, and wherein the specimen cylinder is attached to the frame to be rotated mainly with respect to its central axis;
    wherein the specimen cylinder is connected at an upper part of the specimen cylinder to the frame by at least two rolls; and
    wherein the rolls are mounted bearings which are connected to the frame and adapted to be moved by a regulating device in order to incline the specimen cylinder to a desired position.

12. A device for measuring compaction properties of masses of a specimen of the soil and other masses of the kind, which includes:
- a frame;
- a specimen cylinder for the specimen, wherein the specimen cylinder is attached to the frame and adapted to be rotated with respect to a central axis of the specimen cylinder, and wherein the specimen cylinder is attached to the frame at an incline;
- an upper platen placed over the specimen;
- a lower platen placed below the specimen, wherein the upper platen and the lower platen are inclined with respect to the central axis of the specimen cylinder; and
- pressing device for pressing the upper platen and the lower platen against the specimen.

13. A device according to claim 12 in which the upper platen and the lower platen are horizontal and not inclined.

* * * * *